United States Patent
Sia

(10) Patent No.: US 9,867,936 B2
(45) Date of Patent: Jan. 16, 2018

(54) DRUG INFUSION SYSTEM AND METHOD FOR CONTROLLING BLOOD PRESSURE

(75) Inventor: Tiong-Heng Alex Sia, Singapore (SG)

(73) Assignee: Singapore Health Services Pte Ltd, Singapore (SG)

( * ) Notice: Subject to any disclaimer, the term of this patent is extended or adjusted under 35 U.S.C. 154(b) by 535 days.

(21) Appl. No.: 13/822,599

(22) PCT Filed: Sep. 15, 2011

(86) PCT No.: PCT/SG2011/000314
§ 371 (c)(1),
(2), (4) Date: May 21, 2013

(87) PCT Pub. No.: WO2012/036636
PCT Pub. Date: Mar. 22, 2012

(65) Prior Publication Data
US 2013/0226138 A1    Aug. 29, 2013

Related U.S. Application Data

(60) Provisional application No. 61/382,945, filed on Sep. 15, 2010.

(51) Int. Cl.
*A61M 5/172*  (2006.01)
*A61M 5/142*  (2006.01)
(Continued)

(52) U.S. Cl.
CPC .......... *A61M 5/1723* (2013.01); *A61M 5/142* (2013.01); *A61M 5/1407* (2013.01);
(Continued)

(58) Field of Classification Search
CPC ............... A61M 5/1723; A61M 5/1407; G06F 19/3468; A61B 5/024; A61B 5/021; A61B 5/155
See application file for complete search history.

(56) References Cited

U.S. PATENT DOCUMENTS

| 3,923,060 A | 12/1975 | Ellinwood, Jr. |
| 4,080,966 A | 3/1978 | McNally et al. |

(Continued)

FOREIGN PATENT DOCUMENTS

| CN | 101442930 A | 5/2009 |
| WO | 2006/091650 A2 | 8/2006 |

(Continued)

OTHER PUBLICATIONS

Cyna et al., "Techniques for preventing hypotension during spinal anaesthesia for caesarean section (Review)," *The Cochrane Library*, Issue 11, 2010, 117 pages.

(Continued)

*Primary Examiner* — Bradley Osinski
(74) *Attorney, Agent, or Firm* — Seed IP Law Group LLP

(57) ABSTRACT

Various embodiments relating to a method of controlling the blood pressure of a subject is provided, the method includes generating blood pressure data indicating the blood pressure of the subject, controlling a plurality of pumps to infuse, in dependence on the blood pressure data, drugs into the subject, wherein each of the plurality of pumps is adapted to infuse one out of a plurality of different drugs into the subject, and wherein each of the plurality of different drugs has a particular influence on the blood pressure of the subject, wherein the plurality of pumps is controlled such that, in dependence on the blood pressure data, a mix of drugs is infused into the subject which stabilizes the blood pressure of the subject.

21 Claims, 5 Drawing Sheets

(51) Int. Cl.
    *A61M 5/168*     (2006.01)
    *G06F 19/00*     (2011.01)
    *A61M 5/14*     (2006.01)
    *A61B 5/021*     (2006.01)
    *A61B 5/024*     (2006.01)
    *A61B 5/00*     (2006.01)

(52) U.S. Cl.
    CPC .... *A61M 5/16804* (2013.01); *A61M 5/16827* (2013.01); *A61M 5/16877* (2013.01); *G06F 19/3468* (2013.01); *A61B 5/021* (2013.01); *A61B 5/024* (2013.01); *A61B 5/4821* (2013.01); *A61B 5/4839* (2013.01); *A61M 2005/14208* (2013.01); *A61M 2005/1726* (2013.01)

(56) References Cited

U.S. PATENT DOCUMENTS

| | | | |
|---|---|---|---|
| 4,756,706 | A | 7/1988 | Kerns et al. |
| 5,099,852 | A * | 3/1992 | Meister et al. ............... 600/485 |
| 6,171,255 | B1 | 1/2001 | Ise et al. |
| 6,224,559 | B1 | 5/2001 | Hendriks |
| 7,014,611 | B1 | 3/2006 | Geddes et al. |
| 7,232,435 | B2 | 6/2007 | Hildebrand et al. |
| 2004/0193328 | A1 | 9/2004 | Zaitsu et al. |
| 2006/0253160 | A1 | 11/2006 | Benditt et al. |
| 2009/0326399 | A1 * | 12/2009 | Barrero Batalloso et al. ............... 600/509 |

FOREIGN PATENT DOCUMENTS

| | | |
|---|---|---|
| WO | 2007/047152 A2 | 4/2007 |
| WO | 2007/132379 A2 | 11/2007 |
| WO | WO 2008107127 A1 * | 9/2008 |

OTHER PUBLICATIONS

Dyer et al., "Hemodynamic effects of ephedrine, phenylephrine, and the coadministration of phenylephrine with oxytocin during spinal anesthesia for elective cesarean delivery," Abstract, *Anesthesiology* 111(4):753-765, 2009, 2 pages.

Erkinaro et al., "Effects of ephedrine and phenylephrine on uterine and placental circulations and fetal outcome following fetal hypoxaemia and epidural-induced hypotension in a sheep model," *British Journal of Anaesthesia* 93(6):825-832, 2004.

Hawthorne et al., "Cardiac arrest complicating spinal anaesthesia for caesarean section," *International Journal of Obstetric Anesthesia* 6:126-129, 1997.

Ngan Kee et al.,"Comparison of phenylephrine infusion regimens for maintaining maternal blood pressure during spinal anaesthesia for Caesarean section," *British Journal of Anaesthesia* 92(4):469-474, 2004.

Parker et al., "Cardiopulmonary Arrest in Pregnancy: Successful Resuscitation of Mother and Infant Following Immediate Caesarean Section in Labour Ward," *Aust. NZ Obstet Gynaecol* 36(2):207-210, 1996.

Roberts et al., "Fetal Acidemia Associated With Regional Anesthesia for Elective Cesarean Delivery," *Obstet Gynecol* 85(1):79-83, Jan. 1995.

Roofthooft et al., "Low-dose spinal anaesthesia for Caesarean section to prevent spinal-induced hypotension," *Curr Opin Anaesthesiol* 21:259-262, 2008.

Smiley et al., "$\beta_2$-Adrenoceptor Genotype Affects Vasopressor Requirements during Spinal Anesthesia for Cesarean Delivery," *Anesthesiology* 104:644-650, 2006.

Warwick et al., "Prevention of Hypotension during Spinal Anesthesia for Cesarean Delivery," *Anesthesiology* 103:744-750, 2005.

* cited by examiner

DRUG INFUSION SYSTEM AND METHOD FOR CONTROLLING BLOOD PRESSURE

CROSS-REFERENCE TO RELATED APPLICATION

This application claims the benefit of priority of U.S. provisional application No. 61/382,945 filed Sep. 15, 2010, the contents of it being hereby incorporated by reference in its entirety for all purposes.

FIELD OF THE INVENTION

Various embodiments relate to a method of controlling the blood pressure of a subject, in particular relating to a system of controlling the blood pressure of a subject.

BACKGROUND OF THE INVENTION

Perioperative fluctuations of arterial blood pressure (BP) are common and may be associated with adverse outcomes. Despite many years of research, fluctuations in blood pressure (BP), particularly hypotension due to spinal anaesthesia remains a very significant clinical problem for obstetric patients undergoing Caesarean section. This has been reported to be as high as 90% in otherwise healthy women and may be associated with serious morbidity to mother and fetus (Roofthooft & Van 2008, Smiley et al. 2006). Maternal arterial hypotension decreases uterine perfusion pressure, leading to intrapartum fetal asphyxia and fetal acidosis (Roberts et al. 1995). Severe maternal hypotension also causes maternal cerebral hypoperfusion, resulting in nausea and vomiting. Cases of intractable hypotension and cardiac arrest during spinal anaesthesia for elective caesaraen section have been described (Hawthrone & Lyons 1997, Parker et al. 1996).

Various techniques have been used to prevent and manage hypotension. The results from Cochrane database of systematic reviews showed that none of the interventions such as colloids, ephedrine, phenylephrine or lower leg compression, are effective in eliminating this condition (Cyna et al. 2006). Vasopressors are drugs commonly used to maintain BP but could lead to significant side effects. One of the difficulties is the large inter-individual variability in the severity of BP changes and their response to treatment. The use of untitrated but necessarily high doses of intravenous vasopressor phenylephrine, in conjunction with intravenous fluids, has been proposed to be nearly obviate the risk of hypotension (Ngan Kee et al. 2005) but at the expense of overtreatment (reactive hypertension and compensatory bradycardia). The impact of such an eventuality on the mother and neonate, especially in high risk patients (severe preeclampsia and intra uterine growth retardation) may not be innocuous. Moreover, injudiciously high doses of phenylephrine have been found to compromise uteroplacental circulation (Erkinaro et al. 2004) in spite of the Pyrrhic elimination of hypotension.

Hypotension, for example, blood pressure lower than about 10% of baseline physiologic value of each individual, is a very common side effect in obstetric patients undergoing Caesarean section. This could potentially induce side effects in both mother (nausea, vomiting) and fetus (acidosis) (Ngan Kee et al. 2004). However, the current standard technique using the recommended drug called phenylephrine is well known to result in overtreatment of BP, resulting in a significantly higher than normal BP (reactive hypertension, with BP greater than 20% of baseline) in more than 40% of the patients and reactive slowing of maternal heart rate (bradycardia); these may not be innocuous in high risk patients (Ngan Kee et al. 2005).

One of the main causes of overtreatment of BP is the inability to continuously and reliably measure BP non-invasively. In particular, the use of the conventional method of non-invasive BP monitoring (based on the principle of oscillometry) is limited by the time it takes to inflate and subsequently to deflate the cuffs commonly applied to the arm. The lag period and lack of a 'real-time' measurement of BP will lead to failure to refine and react in a timely manner to changes in BP when they occur. In spinal anaesthesia, these changes could be very drastic and sudden—if left untreated could result in negative repercussions to the mother and fetus. The use of an invasive catheter which is inserted into the artery (arterial line) is impractical and not without risk.

There remains a need to provide an alternative approach that can prevent or ameliorate the adverse clinical outcomes associated with fluctuations of BP.

SUMMARY OF THE INVENTION

In one aspect, the invention provides a method of controlling the blood pressure of a subject. The method includes generating blood pressure data indicating the blood pressure of the subject; controlling a plurality of pumps to infuse, in dependence on the blood pressure data, drugs into the subject, wherein each of the plurality of pumps is adapted to infuse one out of a plurality of different drugs into the subject, and wherein each of the plurality of different drugs has a particular influence on the blood pressure of the subject; wherein the plurality of pumps is controlled such that, in dependence on the blood pressure data, a mix of drugs is infused into the subject which stabilizes the blood pressure of the subject.

In another aspect, the invention provides a system of controlling the blood pressure of a subject. The system comprising a blood pressure data generating unit adapted to generate blood pressure data indicating the blood pressure of the subject; a plurality of pumps, wherein each of the plurality of pumps is adapted to infuse one out of a plurality of different drugs into the subject, each of the plurality of different drugs having a particular influence on the blood pressure of the subject; a controlling unit adapted to control the plurality of pumps to infuse, in dependence on the blood pressure data, a mix of drugs into the subject which stabilizes the blood pressure of the subject.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE INVENTION

Figure 1:
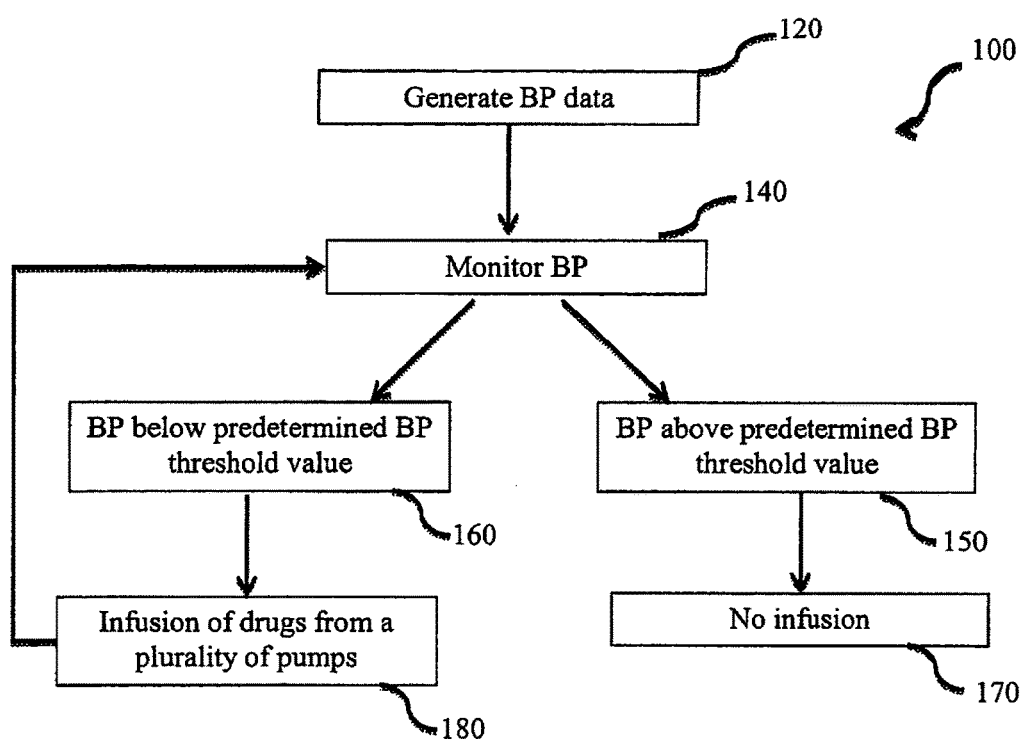
FIG. 1 represents a schematic flow diagram 100 illustrating a method of controlling the blood pressure (BP) of a subject, according to various embodiments.

The following detailed description refers to accompanying drawings that show, by way of illustration, specific details and embodiments in which the invention may be practiced. These embodiments are described in sufficient detail to enable those skilled in the art to practice the invention. Other embodiments may be utilized and structural, logical changes may be made without departing the scope of the invention. The various embodiments are not necessarily mutually exclusive, as some embodiments can be combined with one or more other embodiments to form new embodiments.

In the context of various embodiments, the term "about" or "approximately" as applied to a value may encompass the exact value and a variance of ±5% of the value.

An alternative and individualized approach to maintain hemodynamic stability has been found which can prevent or ameliorate the adverse clinical outcomes associated with fluctuations of blood pressure. Without wishing to be bound by theory, the systolic blood pressure can be maintained within about 10% of the baseline value. Therefore, the neonatal outcomes (APGAR scores, umbilical cord pH) and the profile of maternal side effects (hypotension, hypertension, nausea, vomiting, bradycardia and maternal satisfaction) will favour patients utilizing the methods and systems of the invention compared to those who receive the standard techniques in the art.

The method of controlling the blood pressure of a subject according to various embodiments of the invention is based on the independent control of a plurality of pumps supplying drugs into subject, in dependence on the blood pressure data of the subject.

Various embodiments thus provide a method of controlling the blood pressure of a subject. The method includes generating blood pressure data indicating the blood pressure of the subject; controlling a plurality of pumps to infuse, in dependence on the blood pressure data, drugs into the subject, wherein each of the plurality of pumps is adapted to infuse one out of a plurality of different drugs into the subject, and wherein each of the plurality of different drugs has a particular influence on the blood pressure of the subject; wherein the plurality of pumps is controlled such that, in dependence on the blood pressure data, a mix of drugs is infused into the subject which stabilizes the blood pressure of the subject.

In various embodiments, the plurality of pumps is controlled to infuse drugs into the subject if the blood pressure falls below a predetermined blood pressure threshold value.

The blood pressure of the subject can be determined arithmetically so long as the value is in relation to an average blood pressure value or range. An average blood pressure value can, for example, be calculated from a summation of at least two blood pressure values determined at regular time intervals of about 10, about 15 or about 20 seconds. The blood pressure threshold value of the subject can refer to a baseline blood pressure that is calibrated according to the methods described herein. In various embodiments, the predetermined blood pressure threshold value is below about 90%, for example, about 89%, about 88% about 87%, about 86%, about 85%, about 84%, about 83%, about 82%, about 81%, or about 80% of the normal blood pressure, to mention only a few. Blood pressure is typically represented as systolic pressure over diastolic pressure. The systolic pressure refers to the pressure in the arterial system at its highest, and diastolic pressure refers to the lowest pressure. It is usually measured in mm Hg. Normal pressure is 120/70 on average, but normal for an individual can vary with the height, weight, fitness level, health, emotional state, age, etc., of a person. Although there is no clear dividing line between normal and high blood pressure, "hypotension" can include absolute hypotension as may be defined medically (such as systolic blood pressure below 90 mm Hg). Within the context of various embodiments, the method can comprise treating or preventing hypotension of a subject.

In various embodiments, the method comprises generating heart rate data reflecting a heart rate of the subject, wherein the plurality of pumps is controlled in dependence on the heart rate. The heart rate of the subject can be determined arithmetically so long as the value is in relation to an average heart rate value or range. An average heart rate value can, for example, be calculated from a summation of at least two heart rate values determined at regular time intervals of about 10, about 15 or about 20 seconds.

In various embodiments, a first pump of the plurality of pumps is controlled to infuse a first drug into the subject if the heart rate of the subject exceeds a predetermined heart rate threshold value. The predetermined heart rate threshold value may refer to the heart rate of the subject that is determined before the method of the invention is carried out. The predetermined heart rate threshold value can for example refer to the resting heart rate of a healthy subject. Typically, a normal heart rate in adults is in the range of about 60 to about 80 beats per minute (bpm). Rates below about 60 bpm can be referred to as bradycardia, and rates above 60 bpm can be referred to as tachycardia. In various embodiments, the predetermined heart rate threshold value is below about 60 bpm, for example, about 59 bpm, about 58 bpm, about 57 bpm, about 56 bpm, about 55 bpm, about 54 bpm, about 53 bpm, about 52 bpm, about 51 bpm, about 50 bpm, about 48 bpm, about 45 bpm, about 40 bpm, to mention only a few.

In various embodiments, a second pump of the plurality of pumps is controlled to infuse a second drug into the subject if the heart rate of the subject falls below the predetermined heart rate threshold value.

A plurality of pumps may for example be two, three, four, five six or any higher number of pumps. The pump can refer to any device capable of delivering at least one drug, in particularly a pump that can provide or infuse drug from a syringe for example, in a controlled manner. Each of the plurality of pumps is adapted to infuse at least one out of a plurality of different drugs, that is for example, a first pump of the plurality of pumps is adapted to infuse a first drug; a second pump of the plurality of pumps is adapted to infuse a second drug; a third pump of the plurality of pumps is adapted to infuse a third drug; a fourth pump of the plurality of pumps is adapted to infuse a fourth drug, and so on. The at least one drug to be infused to the subject has a particular influence on the blood pressure of the subject, so long as the blood pressure of the subject is stabilized. The drug can, for example, be any drug that treats or prevents hypotension, any vasopressor drugs including but not limited to phenylephrine, ephedrine and their derivatives thereof.

In various embodiments, the drugs can be injected into the subject continuously in regular time intervals until the blood pressure exceeds the blood pressure threshold value. The regular time intervals can be in the range of between about 10 to 40 seconds, between about 10 to 30 seconds, between about 10 to 20 seconds, between about 15 to 30 seconds, between about 15 to 20 seconds, about 25 seconds, about 20 seconds, about 15 seconds, or about 10 seconds.

In various embodiments, phenylephrine can be injected with a dose of between about 0.01 mg to 0.2 mg; about 0.01 mg to 0.1 mg; about 0.01 mg to 0.05 mg; about 0.025 mg to 0.2 mg; about 0.05 mg to 0.2 mg; about 0.01 mg to 0.2 mg; about 0.1 mg to 0.2 mg; 0.05 mg or 0.025 mg at regular time intervals. In various embodiments, ephedrine can be injected with a dose of between about 0.5 mg to 4 mg; about 0.5 mg to 3.5 mg; about 0.5 mg to 3 mg; about 0.5 mg to 2.5 mg; about 0.5 mg to 2 mg; about 0.5 mg to 1.5 mg; about 0.5 mg to 1 mg; 4 mg, 2 mg or 1 mg at regular time intervals.

In various embodiments, the blood pressure data and the heart rate data are collected in real time. In various embodiments, the blood pressure data is collected using optical sensors. The optical sensors can be integrated into a cuff which is adapted to apply mechanical pressure on the subject.

Various embodiments also provide a system of controlling the blood pressure of a subject. The system includes a blood pressure data generating unit adapted to generate blood pressure data indicating the blood pressure of the subject, a plurality of pumps, wherein each of the plurality of pumps is adapted to infuse one out of a plurality of different drugs into the subject, each of the plurality of different drugs having a particular influence on the blood pressure of the subject, a controlling unit adapted to control the plurality of pumps to infuse, in dependence on the blood pressure data, a mix of drugs into the subject which stabilizes the blood pressure of the subject.

In various embodiments, the blood pressure data generating unit is adapted to generate the blood pressure data in real time. The blood pressure data generating unit can in some embodiments be a non-invasive blood pressure data generating unit, and can for example be a hemodynamic monitoring device. In some embodiments, the blood pressure data generating unit can include optical sensors. The optical sensor can, in some embodiments, be integrated in a cuff wherein the cuff is adapted to apply mechanical pressure onto the subject. Blood pressure can thus be measured by way of an infrared light optical sensor measuring pulse pressure in the subject's fingertip for example. The blood pressure data generating unit can also include a display unit adapted to display the blood pressure data.

In various embodiments, the controlling unit may comprise means for receiving information from the blood pressure data generating unit, and means for sending information to the plurality of pumps. The process and related means may be implemented using hardware, software or a combination thereof and may be implemented, for example, in one or more computer systems or other processing systems.

In various embodiments, the system further includes a heart rate data generating unit adapted to generate heart rate data reflecting heart rate of the subject. The heart rate data generating unit can include any heart rate measuring device for example, heart rate monitor, or pulse oximeter, so long as the heart rate of the subject can be determined.

The controlling unit controls the plurality of pumps in dependence on the heart rate data. In various embodiments, the controlling unit is adapted to control a first pump of the plurality of pumps to infuse a first drug into the subject if the heart rate of the subject exceeds a predetermined heart rate threshold value. In other embodiments, the controlling unit is adapted to control a second pump of the plurality of pumps to infuse a second drug into the subject if the heart rate of the subject falls below the predetermined heart rate threshold value.

In order that the invention may readily understood and put into practical effect, particular embodiments will now be described with reference to the figures. It should also be appreciated that any of the components or sub-components discussed herein with regards to various embodiments of the present invention may be communicated with one another with data or signal transfer via a variety of communication interfaces. For example, in the form of signals or data may be electronic, electromagnetic, optical or other signals capable of being received by communications interface and components and subcomponents of the present invention. The communication may, for example be implemented using serial ports, wire or cable, fiber optics, a phone line, a cellular phone link, or other communication channels (hard wire or wireless included). Similarly, any material, fluid or medium transported between components or subcomponents described herein with regard to the various embodiments of the invention may include a variety of types, such as, but not limited to conduits, tubes, lumen, channels, needles, catheters or the like.

FIG. 1 represents a schematic flow diagram 100 illustrating a method of controlling the blood pressure (BP) of a subject, according to various embodiments. The BP reading of a subject can be taken by a blood pressure data generating unit 120 according to various embodiments of the invention. This subject may for example be a human subject. The subject may for example be a patient undergoing a perioperative procedure. The subject can be an obstetric patient. The BP of the subject is monitored at step 140 and an average BP can be arithmethically calculated based on final three readings of the systolic blood pressure of the subject. When criterion 160 is met, in which the BP falls below a predetermined BP threshold value, the plurality of pumps 180 is controlled to infuse drugs into the subject. When criterion 150 is met, in which BP exceeds the predetermined BP threshold value, the plurality of pumps 170 will be deactivated and no infusion of drugs occur.

Figure 2:
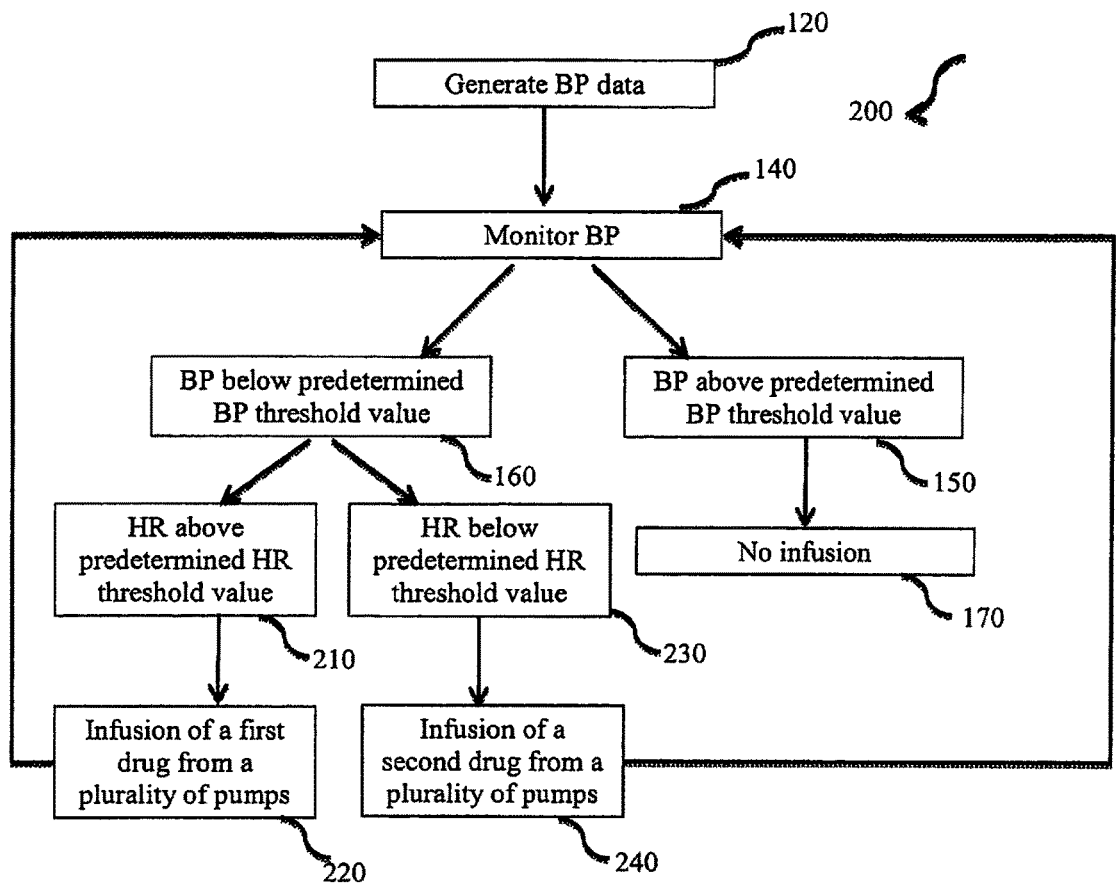
FIG. 2 represents a schematic flow diagram 200 illustrating a method of controlling the blood pressure (BP) of a subject, according to various embodiments. "HR" represents heart rate of the subject.

FIG. 2 represents a schematic flow diagram 200 illustrating a method of controlling the blood pressure (BP) of a subject, according to various embodiments. The BP reading of a subject is taken by a blood pressure data generating unit 120 according to various embodiments of the invention, the BP is monitored and an average BP is determined at step 140. When both criteria 160 and 210 are met in which BP of the subject falls below a predetermined BP threshold value and heart rate (HR) exceeds a predetermined HR threshold value, a first pump 220 of a plurality of pumps is controlled to infuse a first drug. When both criteria 160 and 230 are met in which BP of the subject falls below a predetermined BP threshold value and HR falls below a predetermined HR threshold value, a second pump 240 of a plurality of pumps is controlled to infuse a second drug. When criterion 150 is met, in which BP exceeds the predetermined BP threshold value, the plurality of pumps 170 will be deactivated and no infusion of drugs occur.

Figure 3:
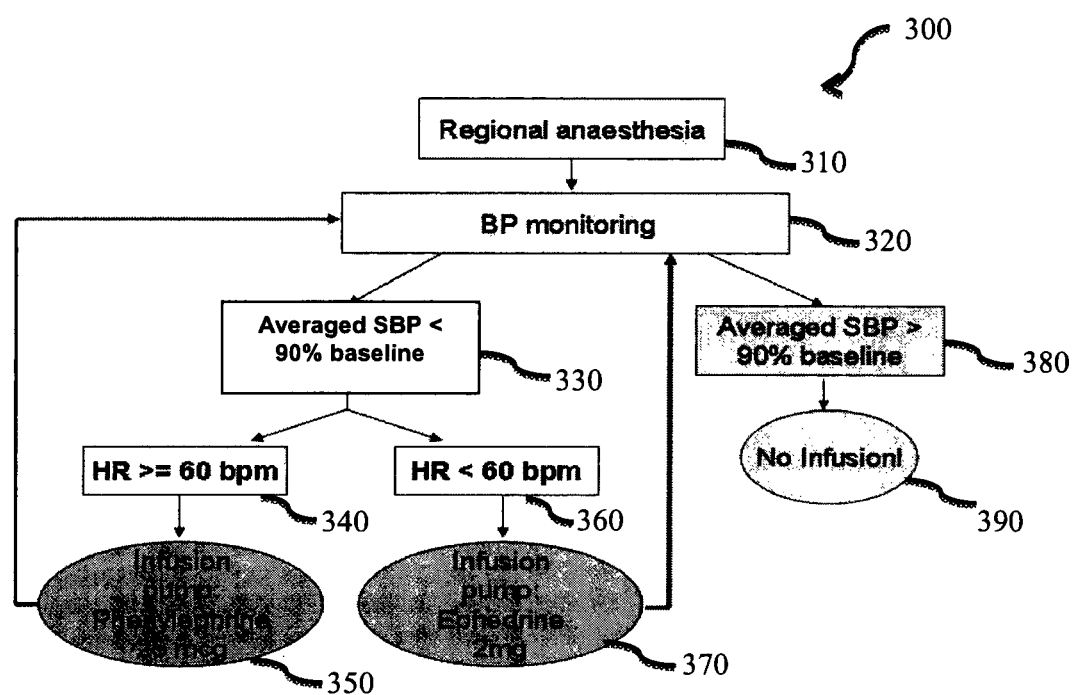
FIG. 3 represents a schematic flow diagram 300 illustrating a method of controlling the blood pressure (BP) of a subject, according to various embodiments. Average blood pressure (BP) is arithmetically calculated based on the last three readings of systolic BP at regular time intervals.

FIG. 3 represents a schematic flow diagram 300 illustrating a method of controlling the blood pressure of a subject, according to various embodiments. Such a method according to various embodiments is carried out with the purpose to maintain the systolic blood pressure (SBP) at 90% of baseline blood pressure. The subject undergoes regional anesthesia 310 and BP is taken and monitored 320. When the SBP of the subject is below 90% of baseline blood pressure 330 and heart rate is below 60 beats per minute 360, both infusion pumps 350 and 370 for phenylephrine 25 mcg and ephedrine 2 mg will be activated. If the heart rate is above or equal to 60 beats per minute 340, only infusion pump 350 for phenylephrine 25 mcg will be activated. On the other hand, if the systolic blood pressure is above 90% of baseline blood pressure 380, neither of the pumps will be activated 390. Without wishing to be bound by theory, the method and system according to the invention provide not only continuous measurements of blood pressure and heart rate without invasive blood pressure monitoring, it also provide instantaneous administration of vasopressors to restore hemodynamic stability.

Figure 4:
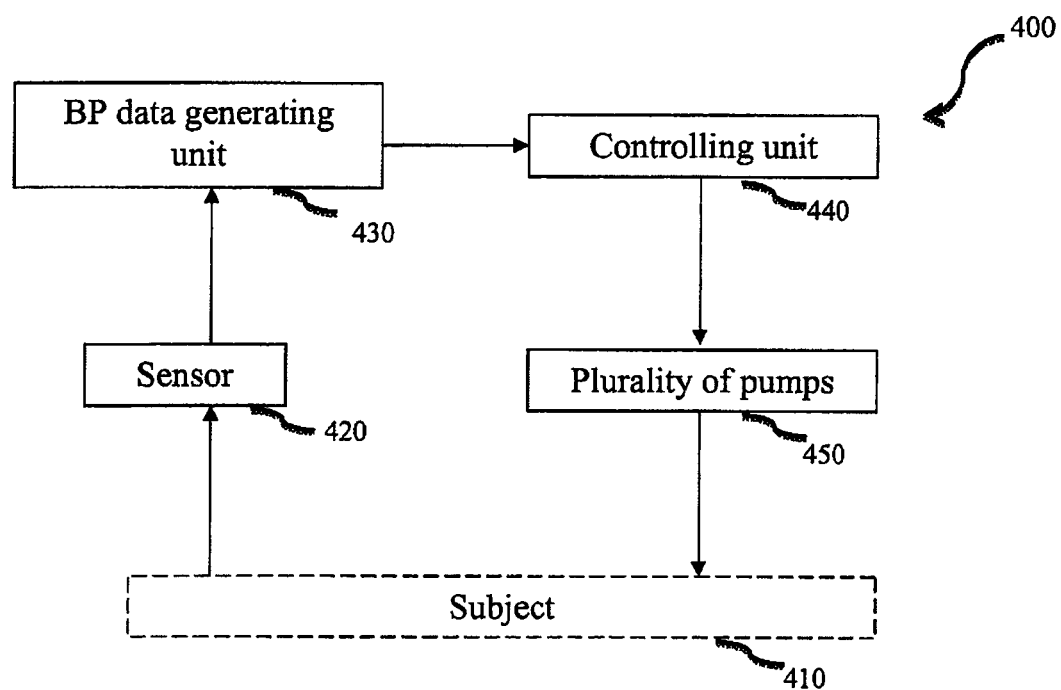
FIG. 4 represents a system 400 for controlling blood pressure of a subject, according to various embodiments.

FIG. 4 illustrates a system 400 for controlling blood pressure of a subject, according to various embodiments. The system can be a closed-loop' dual-pump automated system (CLDPAS) integrated by a method according to various embodiments, to regulate patients' hemodynamic status during anaesthesia. The system can also be operated under a fixed rate mode. The blood pressure of a subject 410 is measured by a sensor 420. The sensor can be integrated into a finger cuff which is adapted to apply mechanical pressure on the subject. Finger cuff from Infinity® CNAP™ SmartPod can be used. The blood pressure data can be displayed by the blood pressure data generating unit 430, and exported continuously to controlling unit 440. The controlling unit 440 may be a computer programmed to implement the methods according to the present invention, provide a user interface and to control communication through serial ports (RS 232) with the blood pressure data generating unit 430 such as the Infinity® CNAP™ hemodynamic Monitor (Draeger Medical, Lubeck, Germany) and the plurality of pumps 450 for example the infusion system (B. Braun, Melsungen AG, Germany). Information will be sent to activate either one of the plurality of pumps 450 or neither based on the methods of the invention. As an illustrative example, the drugs phenylephrine and ephedrine were prepared at a concentration of 100 microgram/ml and 8 mg/ml, respectively, in two 50-ml syringe that was connected via fine-bore extension tubing to the patient's intravenous cannula by a three-way stopcock without using a oneway valve.

Figure 5:
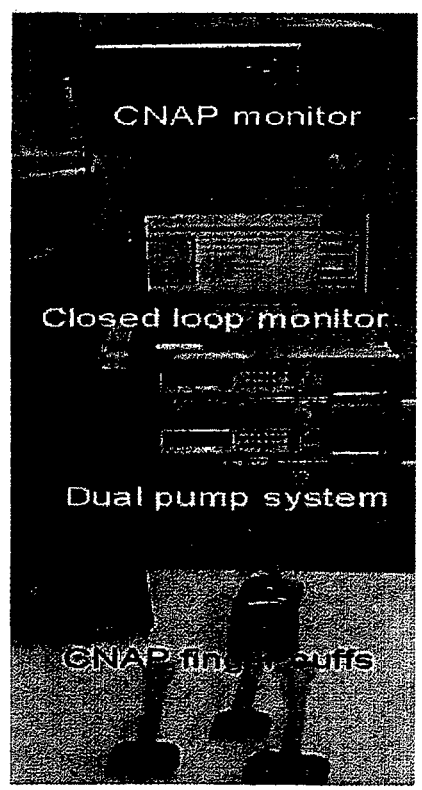
FIG. 5 shows an image displaying the components of a closed-loop' dual-pump automated system (CLDPAS) for controlling the blood pressure of a subject, according to various embodiments. "CNAP" stands for Continuous Non-invasive Arterial Pressure.

FIG. 5 shows an image displaying the components of a closed-loop' dual-pump automated system (CLDPAS) for controlling the blood pressure of a subject, according to various embodiments. "CNAP" stands for Continuous Noninvasive Arterial Pressure.

Figure 6:
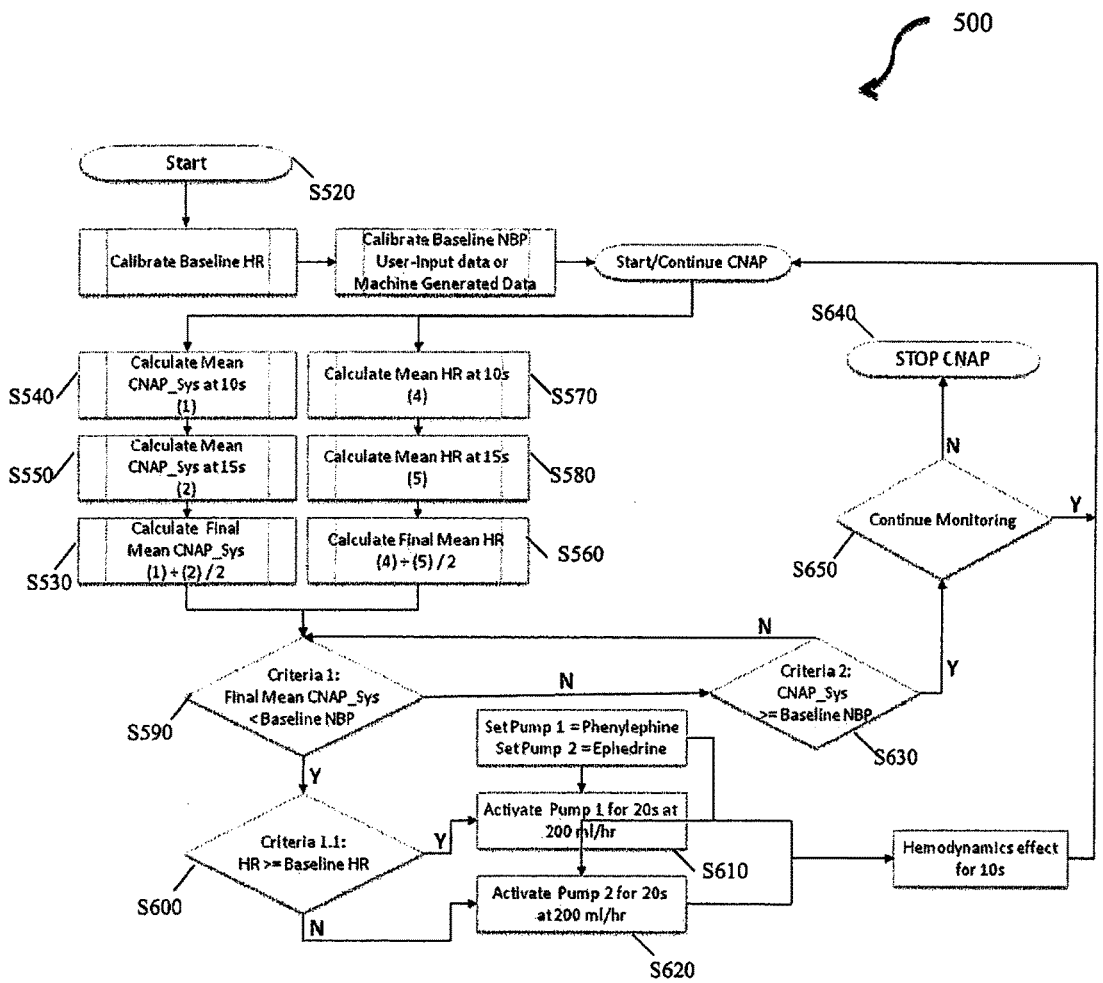
FIG. 6 represents a schematic diagram 500 of a closed-loop controller for infusion of phenylephrine or ephedrine drugs during caesarean section under spinal anaesthesia, according to various embodiments. "CNAP_Sys" represents CNAP Systolic BP (finger); Baseline NBP represents Non-invasive BP (cuff); Baseline HR represents HR before start; Mean CNAP_Sys10s represents Mean CNAP from 1 s to 10 s; Mean CNAP_Sys15s represents Mean CNAP from 10 s to 15 s.

FIG. 6 represents a schematic diagram 500 showing the basic operation of a closed-loop controller for infusion of phenylephrine or ephedrine drugs during caesarean section under spinal anaesthesia, according to various embodiments. The closed-loop' dual-pump automated system (CLDPAS) system utilizes the Infinity® CNAP™ (Continuous Noninvasive Arterial Pressure) SmartPod and the data generated will be fed-back to a microprocessor to tightly regulate the functions of two infusion pumps for drugs to regulate blood pressure, i.e. vasopressors, namely phenylephrine and ephedrine. Infinity® CNAP™ gives an instantaneous, continuous measure for arterial BP. The photoplethysmograph sensors use an infrared light source and a light detector measure the blood volume in the finger arteries and a direct measure of arterial real-time BP is derived from the sensor cuff pressure. This enables BP calculated by beat-to-beat and a high resolution arterial pressure waveform can be obtained to allow a comprehensive view of the patient's status. The maternal systolic BP will be continuously fed back to the computer integrated infusion pumps and in response, a preset volume of vasopressors will be infused. The computer-controlled infusion program used was developed using Microsoft .Net 3.5 under the Windows XP operating system. By user selection, the program can be switched between fixed rate mode and closed-loop feedback mode.

Referring to the schematic diagram of FIG. 6, the basic operation of the system running under closed-loop feedback mode is shown. At step S520, the baseline heart rate ("Baseline HR") and baseline blood pressure ("Baseline NBP") are calibrated. The blood pressure S530 ("Final Mean CNAP_Sys") of a subject is calculated by averaging the total of mean blood pressure value from 1 s to 10 s at step S540 ("Mean CNAP_Sys10s") and mean blood pressure value from 10 s to 15 s at step S550. The heart rate 5560 ("Final Mean HR") of the subject is calculated by averaging the total of mean heart rate value from 1 s to 10 s ("Mean HR at 10 s") at step S570 and mean heart rate value from 10 s to 15 s at step S580 ("Mean HR at 15 s"). If criterion 1 is fulfilled at step S590 in which the blood pressure ("Final Mean CNAP_Sys") of the subject falls below the baseline blood pressure ("Baseline NBP"), and criterion 1.1 is fulfilled at step S600 in which the heart rate (HR) of the subject exceeds or is equal to the baseline heart rate, pump 1 S610 will be activated to infuse phenylephine for 20 s at 200 ml/hr. When criteria 1 is fulfilled at step S590 in which the blood pressure ("Final Mean CNAP_Sys") of the subject falls below the baseline blood pressure ("Baseline NBP") and criteria 1.1 is not fulfilled at step S600 in which the heart rate (HR) of the subject falls below the baseline heart rate, both pump 1 S610 and pump 2 S620 will be activated to infuse phenylephine and ephedrine respectively for 20 s at 200 ml/hr. If criterion 2 is fulfilled at step S630 in which the blood pressure ("Final Mean CNAP_Sys") of the subject exceeds or is equal to the baseline blood pressure ("Baseline NBP"), the pumps will be deactivated and infusion will stop S640. The maternal systolic BP will be monitored S650 and continuously fed back to the computer integrated infusion pumps and in response, a preset volume of vasopressors will be infused.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples as follows. In addition, where features or aspects of the invention are described in terms of Markush groups, those skilled in the art will recognize that the invention is also thereby described in terms of any individual member or subgroup of members of the Markush group.

EXAMPLES

A Closed Loop Dual Pump Automated System (CLDPAS) arterial pressure control system integrated by a unique clinical algorithm to allow a greater control patients' hemodynamic status during anaesthesia is developed. This system utilizes the Infinity® CNAP™ (Continuous Noninvasive Arterial Pressure) SmartPod whereby the data generated will be fed-back to a microprocessor to tightly regulate the functions of two infusion pumps for drugs to regulate blood pressure, i.e. vasopressors, namely, phenylephrine and ephedrine, via a custom-made USB connection.

CLDPAS is able to continuously and accurately measure beat-to-beat arterial BP via a non-invasive monitor plus automate and refine the infusion of vasopressors through computer integrated infusion pumps.

The preliminary prospective cohort study was conducted to assess the efficacy of the CLDPAS arterial pressure control system to treat hypotension during a standardised spinal anaesthetic for Caesarean delivery.

Methods

Institutional approval was obtained from Singapore Health Services Centralised Institutional Review Board. The CLDPAS arterial pressure system was developed by Professor Alex Sia.

41 women were recruited in this preliminary study. The inclusion criteria included ASA 1 and 2 women and term singleton pregnancies scheduled for an elective caesarean section under spinal anaesthesia. Women with pre-existing or pregnancy-induced hypertension, cardiovascular or cerebrovascular diseases, known foetal abnormality or any signs of onset of labour were not included. Oral premedication with sodium citrate 0.3M was given prior to arrival at the operating theatre. A baseline systolic blood pressure was calculated as the mean of three recordings and this value was used as the target systolic blood pressure in the CLDPAS arterial pressure system. An 18G cannula was inserted into a forearm vein under local anaesthesia and connected this to a 500 ml Hartmann's solution bag suspended about 1.5 m above the operating table. Blood (3 mls) was withdrawn and collected in the EDTA tube for the genetic arm of the study (genotyping for adrenoceptor genetic polymorphism).

All subjects were monitored by electrocardiography, pulse oximetry and blood pressure assessment with the Infinity CNAP system. No intravenous prehydration was given. The woman would be placed in the sitting position for induction of spinal anaesthesia. After skin infiltration with lignocaine, a 27G pencilpoint needle was inserted at the L3-L4 interspace and 2.2 ml 0.5% hyperbaric bupivacaine with 15 mcg fentanyl and 100 mcg morphine was administered intrathecally. The patient was immediately returned to the tilted supine position. Directly after the intrathecal injection, the CLPAS arterial pressure system and rapid intravenous fluid infusion (coloading) was initiated.

The system integrates a unique clinical algorithm using the Infinity CNAP to a microprocessor to regulate blood pressure by treating hypotension by activating vasopressor infusion pumps. Phenylephrine bolus of 50 mcg will be activated when the systolic blood pressure is reduced by more than 10% of the baseline systolic blood pressure without bradycardia i.e heart rate less than 60 beats per minute. Ephedrine bolus of 4 mg will be activated when the systolic blood pressure is reduced by more than 10% of the baseline blood pressure associated with bradycardia. The attending anaesthetist was allowed to give additional boluses of phenylephrine, ephedrine or atropine if there was severe hypotension (systolic blood pressure less than 65 mmHg) or severe bradycardia (heart rate less than 45 bpm).

The dermatomal level of loss of cold sensation is taken at 5 minutes after intrathecal injection. Adverse effects such as nausea and vomiting would also be reported. Demographic data such as age, weight, height, baseline systolic blood pressure and baseline heart rate were recorded. Clinical outcomes including time of intrathecal injection, time of lying in supine position, time of skin incision, time of delivery, time of end of surgery, dose of phenylephrine and ephedrine before delivery, total dose of phenylephrine and ephedrine, total volume of intravenous fluid, maximum and minimum systolic blood pressure, maximum and minimum heart rate, APGAR score at 1 and 5 minutes and birthweight were also recorded.

Statistical analyses in this study were performed using SPSS 16.0. The demographic data and characteristics of the patients were analysed using median [range][interquartile range] and mean (standard deviation). The clinical outcomes of the patients were analysed using median [range][interquartile range]. The incidence of phenylephrine and ephedrine requirement and side effects (nausea, vomiting) were reported as number (percentage).

Results

Forty one patients completed the preliminary study with no drop-outs. There were no failures from the spinal anaesthesia requiring conversion to general anaesthesia. The characteristics of the patients were summarized in Table 1.

Thirty eight patients (92.6%) required phenylephrine throughout the caesarean delivery. Thirty seven (90.2%) required phenylephrine before the fetus delivery. Ten patients (24.4%) required ephedrine during the Caesarean delivery. Eight patients required ephedrine before delivery. Two patients experienced nausea during the Caesarean section, but no patients had any episode of vomiting. The attending anaesthetist did not need to administer additional phenylephrine, ephedrine or atropine.

The clinical outcomes of the patients are summarized in Table 2.

All 41 patients agreed for the genetic screening for adrenoceptor genetic polymorphism. The blood samples were collected during intravenous cannulation using EDTA tubes.

Discussion

A Closed Loop Dual Pump Automated System (CLDPAS) arterial pressure control system for maintaining maternal blood pressure during spinal anaesthesia for caesarean section according to various embodiments of the invention is described herein. The present system did not require any additional intervention from the anesthetist and resulted in good clinical outcomes for the women and baby. A minority of women (4.9%) experienced nausea during the caesarean section. There was no occurrence of vomiting and all babies had APGAR 9 at 5 minutes.

Most patients required the phenylephrine automated boluses from the CLDPAS arterial pressure system during the Caesarean section. The CLDPAS arterial pressure system has the unique ability to infuse automated ephedrine boluses. Eight out of 41 patients (19.5%) had bradycardia associated with hypotension that required ephedrine boluses. Without wishing to be bound by theory, this finding suggests that the dual pump setup according to various embodiments of the invention is useful to counteract the effects of hypotension and bradycardia that may coexist under these circumstances. The ability of CLDPAS to rapidly and effectively respond to hemodynamic changes is facilitated by the Infinity CNAP system that enables a near continuous non-invasive monitoring of systolic blood pressure when compared to the currently available systems that provide only intermittent blood pressure readings. As a corollary, the concept CLDPAS would also be applicable to any system that enables either invasive (achieved by transduction via an intraarterial catheter) or non-invasive continuous blood pressure monitoring devices. On the other hand, the often used intermittent non-invasive blood pressure monitoring (typically undertaken by using a repeatedly inflating a cuff on the arm and commonly based on the principle of oscillometry) is unable to perform reliably if the frequency between two measurements is shorter than 1-minute, even if the process can fully automated. It is also more prone to artefacts such as shivering. The CLDPAS arterial pressure system would average the systolic blood pressure readings over each 15 second epochs to allow an almost 'real time' response to changes of blood pressure below the 10% of the baseline value.

As the reference of the Infinity CNAP was based on the conventional non-invasive blood pressure monitoring, the Infinity CNAP was recalibrated every 10-15 minutes. Therefore the CLDPAS according to the invention is found as a reliable arterial pressure control system during spinal anaesthesia for caesarean section.

TABLE 1

Characteristics of patients undergoing Caesarean section with CLDPAS arterial pressure system. Values are median [range] or mean (SD).

| | |
|---|---|
| Age; years | 32.9 (5.0) |
| Weight; kg | 68.1 (10.4) |
| Height; cm | 159.0 (5.4) |
| Baseline systolic blood pressure; mmHg | 123 [104-140][116-131] |
| Baseline heart rate; bpm | 78 [65-97][70-85] |

TABLE 2

Clinical outcomes of patients undergoing Caesarean section with CLDPAS arterial pressure system. Values are median [range][IQR].

| | |
|---|---|
| Block height at 5 minute; dermatome | T3 [T1-T6] |
| Spinal to supine position time; min | 2 [1-6] |
| Spinal to delivery time; min | 17 [9-46] |
| Spinal to end of surgery time; min | 43 [28-107] |

TABLE 2-continued

Clinical outcomes of patients undergoing Caesarean section with CLDPAS arterial pressure system. Values are median [range][IQR].

| | |
|---|---|
| Dose of phenylephrine before delivery; mcg | 250 [0-1200] |
| Dose of ephedrine before delivery; mg | 0 [0-24] |
| Total dose of phenyleprine; mcg | 800 [0-2150] |
| Total dose of ephedrine; mg | 0 [0-28] |
| Total fluids; mls | 1500 [1000-2500] |
| Maximum systolic blood pressure; mmHg | 130 [109-157] |
| Maximum heart rate; bpm | 108 [82-153] |
| Minimum systolic blood pressure; mmHg | 84 [69-125] |
| Minimum heart rate; bpm | 59 [47-85] |
| APGAR score at 1 min | 9 [6-9] |
| APGAR score at 5 min | 9 [9-9] |
| Birthweight; gm | 3145 [2426-4642] |

REFERENCES

Cyna A M, Andrew M, Emmett R S, Middleton P, Simmons S W. Techniques for preventing hypotension during spinal anaesthesia for caesarean section. *Cochrane Database Syst Rev,* 2006(4):CD002251.

Erkinaro T, Mäkikallio K, Kavasmaa T, Alahuhta S, Räsänen J. Effects of ephedrine and phenylephrine on uterine and placental circulations and fetal outcome following fetal hypoxaemia and epidural-induced hypotension in a sheep model. *Br J. Anaesth.* 2004. 93(6):825-32.

Hawthorne, L. and Lyons G. Cardiac arrest complicating spinal anaesthesia for caesarean section. Int J Obstet Anesth, 1997. 6(2):126-9.

Ngan Kee W D, Khaw K S, Ng F F. Comparison of phenylephrine infusion regimens for maintaining maternal blood pressure during spinal anaesthesia for Caesarean section. *Br J. Anaesth.* 2004. 92(4):469-74.

Ngan Kee W D, Khaw K S, Ng F F. Prevention of hypotension during spinal anesthesia for cesarean delivery: an effective technique using combination phenylephrine infusion and crystalloid cohydration. *Anesthesiology.* 2005. 103 (4):744-50.

Parker J, Balis N, Chester S, Adey D. Cardiopulmonary arrest in pregnancy: successful resuscitation of mother and infant following immediate caesarean section in labour ward. *Aust N Z J Obstet Gynaecol,* 1996. 36(2): 207-10.

Roberts S W, Leveno K J, Sidawi J E, Lucas M J, Kelly M A. Fetal acidemia associated with regional anesthesia for elective cesarean delivery. *Obstet Gynecol,* 1995. 85(1): 79-83.

Roofthooft, E. and M. Van de Velde, Low-dose spinal anaesthesia for Caesarean section to prevent spinal-induced hypotension. *Curr Opin Anaesthesiol,* 2008. 21(3): 259-62.

Smiley R M B J, Negron M, Landau R. beta2-adrenoceptor genotype affects vasopressor requirements during spinal anesthesia for cesarean delivery. *Anesthesiology,* 2006. 104(4):644-50.

What is claimed is:

1. A method of controlling a blood pressure of a subject, comprising:
 (a) calibrating a blood pressure baseline for the subject;
 (b) selecting a blood pressure threshold corresponding to said blood pressure baseline;
 (c) calibrating a heart rate baseline for the subject;

(d) selecting a heart rate threshold corresponding to said heart rate baseline;

(e) calculating a final mean blood pressure indicating the blood pressure of the subject during a pre-determined period, wherein the blood pressure is generated by a non-invasive blood pressure data generating unit such that calculating the final mean blood pressure includes the step of applying a greater weight to blood pressure measured in a later part of the pre-determined period than during an earlier part, wherein the earlier part of the pre-determined period is longer than the later part of the pre-determined period and wherein the step of applying a greater weight to blood pressure measured in the later part of the pre-determined period comprises the steps of:

(i) calculating an earlier part mean blood pressure from blood pressure readings for each second up to the end of the earlier part of the pre-determined period to obtain the earlier part mean blood pressure;

(ii) calculating a later part mean blood pressure from blood pressure readings for each second during the later part of the pre-determined period to obtain the later part mean blood pressure: and then (iii) calculating the final mean blood pressure as an average of the earlier part mean blood pressure and the later part mean blood pressure;

(f) generating heart rate data indicating a heart rate of the subject;

(g) controlling a plurality of pumps to infuse drugs into the subject, wherein each of the plurality of pumps is adapted to infuse one out of a plurality of different drugs into the subject, and wherein each of the plurality of different drugs has a particular influence on the blood pressure of the subject;

wherein the plurality of pumps is controlled such that, in dependence on the final mean blood pressure relative to the blood pressure threshold and the heart rate data relative to the heart rate threshold, a mix of drugs is infused into the subject which stabilizes the blood pressure of the subject, wherein the plurality of pumps is controlled to infuse drugs into the subject if the blood pressure of the subject falls below the blood pressure threshold, wherein the injection of drugs into the subject is continued in regular time intervals ranging between 15 and 30 seconds until the blood pressure exceeds the blood pressure threshold.

2. The method according to claim 1, wherein the blood pressure threshold is below 90% of a baseline blood pressure.

3. The method according to claim 1, wherein a first pump of the plurality of pumps is controlled to infuse a first drug into the subject if the heart rate of the subject exceeds the heart rate threshold.

4. The method according to claim 3, wherein the first drug is Phenylephrine.

5. The method according to claim 4, wherein Phenylephrine is injected with a dose of between about 0.01 mg to 0.2 mg or 0.025 mg at regular time intervals.

6. The method according to claim 1, wherein a second pump of the plurality of pumps is controlled to infuse a second drug into the subject if the heart rate of the subject falls below the heart rate threshold.

7. The method according to claim 6, wherein the second drug is Ephedrine.

8. The method according to claim 7, wherein Ephedrine is injected with a dose of between about 0.5 mg to 4 mg or 2 mg at regular time intervals.

9. The method according to claim 1, wherein the heart rate threshold is below 60 beats per minute.

10. The method according to claim 1, wherein the blood pressure data and/or heart rate data is collected in real time.

11. The method according to claim 1, wherein the calibrating step includes the steps of taking 3 blood pressure readings from the subject and calculating an average of said readings.

12. The method according to claim 1, wherein the pre-determined period is 15 seconds with the earlier part of the period being up to 10 seconds and the later part being from 10 to 15 seconds, and the step of applying a greater weight including the steps of:

calculating a 1 to 10 second mean blood pressure from blood pressure readings for each second up to 10 seconds and;

calculating a 10 to 15 second mean blood pressure from blood pressure readings for each second from 10 to 15 seconds, then;

calculating the final mean blood pressure from the average of the 1 to 10 second mean and the 10 to 15 second mean.

13. A system of controlling a blood pressure of a subject, comprising:

(a) a blood pressure data generating unit adapted to generate blood pressure data indicating the blood pressure of the subject, and further adapted to calibrate a blood pressure baseline for the subject and select a blood pressure threshold corresponding to said blood pressure baseline, wherein the blood pressure data generating unit is non-invasive and wherein said blood pressure data generating unit is adapted to calculate a final mean blood pressure pressure indicating the blood pressure of the subject during a pre-determined period such that the final mean blood pressure includes a greater weight to blood pressure measured in a later part of the pre-determined period than during an earlier part of the pre-determined period, wherein calculating the final mean blood pressure includes the step of applying a greater weight to blood pressure measured in a later part of the pre-determined period than during an earlier part of the pre-determined period, wherein the earlier part of the pre-determined period is longer than the later art of the pre-determined period and wherein the step of applying a greaer weight to blood pressure measured in the later part of the pre-determined period comprises the steps of:

(i) calculting an earlier part mean blood pressure from blood pressure readings for each second up to the end of the earlier part of the pre-determined period to obtain the earlier part mean blood pressure;

(ii) calculating a later part mean blood pressure from blood pressure readings for each second during the later part of the pre-determined period to obtain the later part mean blood pressure; and then (iii) calculating the final mean blood pressure as an average of the earlier part mean blood pressure and the later part mean blood pressure;

(b) a heart rate data generating unit adapted to generate heart rate data indicating a heart rate of the subject, and further adapted to calibrate a heart rate baseline for the subject and select a heart rate threshold corresponding to said heart rate baseline;

(c) a plurality of pumps, wherein each of the plurality of pumps is adapted to infuse one out of a plurality of different drugs into the subject, each of the plurality of different drugs having a particular influence on the blood pressure of the subject;

(d) a controlling unit adapted to control the plurality of pumps to infuse, in dependence on the final mean blood pressure relative to the blood pressure threshold and the heart rate data relative to the heart rate threshold, a mix of drugs into the subject which stabilizes the blood pressure of the subject, wherein the plurality of pumps are controlled such that drugs are infused into the subject if the blood pressure of the subject falls below the blood pressure threshold, wherein the controlling unit is adapted to cause the injection of drugs into the subject in regular time intervals ranging between 15 and 30 seconds until the blood pressure exceeds the blood pressure threshold.

14. The system according to claim 13, wherein the blood pressure threshold falls below 90% of a baseline blood pressure.

15. The system according to claim 13, wherein the controlling unit is adapted to control a first pump of the plurality of pumps to infuse a first drug into the subject if the heart rate of the subject exceeds the heart rate threshold.

16. The system according to claim 15, wherein the first drug is Phenylephrine.

17. The system according to claim 16, wherein the controlling unit is adapted to cause injection of Phenylephrine with a dose of between about 0.01 mg to 0.2 mg or 0.025 mg at regular time intervals.

18. The system according to claim 13, wherein the controlling unit is adapted to control a second pump of the plurality of pumps to infuse a second drug into the subject if the heart rate of the subject falls below the heart rate threshold.

19. The system according to claim 18, wherein the second drug is Ephedrine.

20. The system according to claim 19, wherein the controlling unit is adapted to cause injection of Ephedrine with a dose of between about 0.5 mg to 4 mg or 2 mg at regular time intervals.

21. The system according to claim 13, wherein the heart rate threshold falls below 60 beats per minute.

* * * * *

UNITED STATES PATENT AND TRADEMARK OFFICE
CERTIFICATE OF CORRECTION

PATENT NO. : 9,867,936 B2  
APPLICATION NO. : 13/822599  
DATED : January 16, 2018  
INVENTOR(S) : Tiong-Heng Alex Sia Page 1 of 1

It is certified that error appears in the above-identified patent and that said Letters Patent is hereby corrected as shown below:

In the Claims

Column 14, Line 34:
"calculate a final mean blood pressure pressure indicating" should read, --calculate a final mean blood pressure indicating--.

Column 14, Lines 45-46:
"period is longer than the later art of the pre-determined period and wherein the step of applying a greaer weight" should read, --period is longer than the later part of the pre-determined period and wherein the step of applying a greater weight--.

Signed and Sealed this  
Third Day of July, 2018

Andrei Iancu  
*Director of the United States Patent and Trademark Office*